United States Patent [19]

Gomez

[11] Patent Number: 4,460,571

[45] Date of Patent: Jul. 17, 1984

[54] COSMETIC COMPOSITION

[76] Inventor: Dominador S. Gomez, 623 Chesapeake Dr., Bolingbrook, Ill. 60439

[21] Appl. No.: 363,038

[22] Filed: Mar. 29, 1982

[51] Int. Cl.$^3$ .............. A61K 7/06; A61K 7/09; A61K 7/11; A61K 47/00

[52] U.S. Cl. .......................... 424/71; 424/70; 424/359

[58] Field of Search ............... 424/71, 70, 359

[56] References Cited

U.S. PATENT DOCUMENTS

| | | | |
|---|---|---|---|
| 2,023,125 | 12/1935 | Dryfuss et al. | 424/359 |
| 3,548,056 | 12/1970 | Eigen et al. | 424/171 |
| 3,898,032 | 8/1975 | Edman et al. | 424/359 |
| 3,904,748 | 9/1975 | Eckert et al. | 424/71 |
| 3,959,491 | 5/1976 | Young et al. | 424/359 |
| 4,087,555 | 5/1978 | Barnett et al. | 424/359 |
| 4,115,548 | 9/1978 | Marsh et al. | 424/70 |
| 4,148,875 | 4/1979 | Barnett et al. | 424/359 |
| 4,195,077 | 3/1980 | Marsh et al. | 424/359 |

*Primary Examiner*—Sam Rosen
*Assistant Examiner*—Freda L. Abramson
*Attorney, Agent, or Firm*—Norman B. Rainer

[57] ABSTRACT

A cosmetic composition usefully applied to human hair and skin is comprised of a homogeneous mixture of milk solids, ethanol, water and volatile fragrances. The composition is non-flammable, and stable toward microbial degradation. The ethanol provides a cooling and antiseptic effect on the skin, promotes rapid hair bonding, and serves as a preservative for the composition.

6 Claims, No Drawings

COSMETIC COMPOSITION

BACKGROUND OF THE INVENTION

1. Field of the Invention

This invention relates to a composition which can be utilized with benefical effects as a face lotion and hairdressing.

2. Prior Art

Cosmetic compositions, and in particular cosmetic creams and lotions, are applied to the skin for a number of purposes—for example, to lubricate or moisturize the skin, to alleviate or compensate for excessively dry or oily skin, to provide a foundation for other cosmetic preparations and the like. Depending upon their intended purposes, such compositions are required to meet certain criteria established by the formulator with respect to stability, shelf life and emollient properties (for example, lubricity, smoothness, body, lipids-to-water ratio and the like), and these determine the kinds and quantities of the ingredients that go into the compositions.

Milk products such as whole fluid milk, skim or nonfat milk, and dry milk solids have long been recognized as having beneficial effects in cosmetic compositions. However, milk contains a variety of natural enzymes and is a rich nutrient for the growth of bacteria and other organisms which contribute to the rapid souring and short shelf life of fluid milk and products containing fluid milk. As a result, milk cannot be employed in cosmetic compositions which are normally stored at room temperature and are required to have a useful shelf life of several years or more.

The souring and spoilage of fluid milk can be inhibited and its shelf life extended by such treatment as pasteurization or sterilization (especially, pasteurization under conditions which insure the complete destruction of all enzymes and microorganisms contained in the milk) if the pasteurized and sterilized milk is stored under refrigeration and consumed within a few days, or a few weeks, of the treatment. However, it has not heretofore been possible to employ fluid milk in ordinary cosmetic compositions, even if the milk is pasteurized or sterilized, because of the necessity for storing such compositions at room temperature for long periods of time.

The spoilage of fluid milk can also be inhibited by the inclusion of large dosages of anti-enzyme (anti-oxidants), bactericidal and fungicidal agents in the milk. However, the anti-enzyme, bactericidal and fungicidal agents heretofore employed (for example, formaldehyde and sodium bisulfite) are either powerful skin irritants or allergents or must be used in such large amounts that the resulting milk product is unsuitable for use in or as a cosmetic. At best, only a very small amount of fluid milk (less than 10%) treated with conventional preservatives can be incorporated in cosmetic compositions before the quantity of preservative agent required to be present reaches unacceptable levels.

Hairdressing formulations which facilitate combing, and cause the combed hair to stay in place are well known. Such formulations, however, are not generally applied to the skin in the same manner as cosmetic compositions. A composition useful both as a hairdressing and skin conditioner would be particularly desirable, especially if the composition is based primarily upon ingredients having assured acceptability by virtue of established history of use on human skin and hair.

It is an object of the present invention to provide a composition which provides an antiseptic, cooling and fragrant effect when applied to human skin, and further provides a holding effect when applied to human hair.

It is a further object of this invention to provide a composition having the aforesaid properties and comprised of ingredients having a proven record of safety for use on human skin and hair.

It is another object of this invention to provide a composition having the aforesaid properties and which is storage stabel and non-flamable.

It is a still further object of this invention to provide a composition of the aforesaid nature which can be easily produced from inexpensive ingredients.

These objects and other objects and advantages of the invention will be apparent from the following description.

SUMMARY OF THE INVENTION

The above and other beneficial objects and advantages are accomplished in accordance with the present invention by a homogeneous fluid composition comprising critically selected relative amounts of milk, ethanol, and volatile fragrances.

The composition acts as a topic lotion on the hair because it facilitates combing. Hair having been treated with the composition and combed or brushed to a desired configuration, will hold said configuration, resisting dishevelment even by a gusty wind. When applied to the face as an after-shaving lotion, the composition provides desired antiseptic, cooling and fragrant effects.

The milk utilized in the composition of this invention is cow's milk commercially sold in high fat, low fat and nonfat modifications. The nonfat variety of milk is preferred because it avoids the possible formation of a creamy coagulum which may adhere to the walls of a confining bottle. Another preferred milk variety useful in the composition of this invention is reconstituted liquid milk made by the addition of water to nonfat dry milk.

Whole milk, produced by a dairy cow, generally contains between about 5.4% and 3.4% fat, and between about 12.2% and 14.9% total solids. Milk products having a lowered fat content are produced by centrifugal separation and removal of various amounts of fat from the whole milk. "Nonfat" varieties of milk have a fat content as low as about 0.1%. The production of dried milk products is generally achieved by thermal evaporation of the water content of the liquid milk precursor. Dried milk products are in widespread commercial use because of their improved keeping qualities and reduced shipping weight.

DESCRIPTION OF THE PREFERRED EMBODIMENT

The composition of the present invention is critically formulated so that the relative amounts of the several ingredients, expressed on a parts by weight basis, are as follows:

| | |
|---|---|
| milk solids | 15–30 |
| water | 140–180 |
| ethanol | 15–35 |
| fragrance | 0.1–1.0 |

The water content of the composition is generally provided by virtue of the water contents of the milk ingredient and alcohol ingredient utilized.

When the composition is formulated in accordance with the above criteria, it is found to be stable toward microbial degradation for more than a year's storage at room temperature, and the composition is non-flammable. If unduly large amounts of alcohol are employed, beyond the ranges of values cited above, the composition becomes flammable. If too little alcohol is utilized, the composition loses its stability toward microbial degradation. A further critical function of the alcohol ingredient is in facilitating evaporation of the volatile content of the composition, causing rapid deposition of the milk solids in a bonding manner on hair, and providing an evaporative cooling effect.

For satisfactory stability properties, it is preferred that the weight ratio of milk solids to alcohol be within the range of 0.5–1.5. In order for the composition to provide adequate but not excessive hair-bonding abilities, it is preferred that the composition contain between 5% and 15% of milk solids. The term "milk solids" denotes that component of milk which is substantially non-volatile at 100° C.

The ethyl alcohol utilized in producing the composition of this invention may be provided by the several grades of ethanol and ethanol/water mixtures industrially available. Various pharmaceutically approved grades of denatured ethanol may be employed.

It has been found that, at the instant of admixture, the composition should contain at least about 20% water to avoid formation of an irreversible precipitate. Said precipitate, representing a denaturization of the protein component of the milk, would form if, for example, liquid milk were slowly added to absolute ethanol. The reverse order of mixing, namely the slow addition of absolute ethanol to liquid milk, with good stirring, will not ordinarily produce a precipitate because of the presence of adequate amounts of water.

When properly formulated in accordance with the quantitative limits cited above, the composition is easily made by a simple mixing operation to form a homogeneous mixture. The term "homogeneous", as used herein, denotes a composition whose physical and chemical properties are uniform throughout. When properly formulated, the composition remains homogeneous for one to three years at ambient room temperature, and longer if refrigerated. If improperly formulated, the composition will either be non-homogeneous at the outset, or will in short time undergo physical changes causing separation of ingredients to produce a heterogeneous mixture. The ingredients most susceptible to separation are the fat and protein contents of the milk.

The fragrance utilized in the composition may be selected from those formulations readily available and known to be pharmacologically safe for use on the hair or skin.

The following examples illustrate some preferred embodiments of this invention and are not intended to limit the invention in any manner.

EXAMPLE 1

Thirty cubic centimeters of a mixture of 70% ethyl alcohol and about 30% water were placed in a clean vessel. Two cubic centimeters of BRUT men's cologne, a product whose trademark is registered by Faberge, Inc. of Minnesota (comprised of 60% alcohol, 30% water and 10% volatile organics) were added to the vessel. One hundred and eighty cubic centimeters of pasteurized milk of 13.1% solids and 2% fat content were then slowly added to the vessel with continuous stirring.

A non-flammable homogeneous mixture is thereby produced which is bottled for commercial distribution.

In transforming volumetric quantities to weight quantities for the purpose of this invention, the specific gravity of milk can be taken to be 1.032 grams/cc. The specific gravity of alcohol/water mixtures can be determined either by measurement with a hydrometer or by consulting various reference tables, one such table being found on page 365 of Volume 9 of the Encyclopedia of Chemical Technology, Kirk-Othmer, 3rd Edition, published by Wiley-Interscience 1980. Reference to said table indicates that the specific gravity of the alcohol/water mixture employed in this example is 0.889 grams/cc.

Accordingly, the composition of this example, expressed on a weight basis is as follows:

| Ingredient | Grams |
|---|---|
| milk solids | 24.3 |
| water | 170.0 |
| ethanol | 19.7 |
| fragrance | 0.15 |

The weight ratio of milk solids to alcohol is 1.23. The composition contains 11.3% by weight of milk solids.

The composition of this example is found to be effective as a hairdressing in facilitating the combing or brushing of the hair. With the rapid evaporation of the alcohol, the hair is caused to be lightly bonded in place so that it is not easily disheveled. The bonding of the hair is not so strong that subsequent combing cannot be carried out.

When applied to the facial skin as an after-shaving lotion, the composition provides a refreshing, antiseptic effect, and appears to stop the bleeding of minor facial cuts.

The composition, stored in a sealed bottle is found to be stable with respect to microbial degradation and de-homogenization for at least a year at ambient room temperature (70° F.).

EXAMPLES 2–6

Employing the mixing process of Example 1, the following formulations were made wherein Examples 2 and 3 utilize the milk ingredient of Example 1, Example 4 employs a liquid milk of high fat content, Example 5 utilizes a liquid "nonfat" milk of 0.1% fat content, and Example 6 employs a reconstituted nonfat dry milk:

| | Grams | | | | |
|---|---|---|---|---|---|
| Ingredient | Example 2 | Example 3 | Example 4 | Example 5 | Example 6 |
| milk solids | 24.3 | 24.3 | 24.3 | 24.3 | 32.2 |
| water | 171.5 | 173.5 | 168.5 | 168.5 | 224.5 |
| ethanol | 36.6 | 46.0 | 27.7 | 27.7 | 37.0 |
| fragrance | 0.1 | 0.1 | 0.1 | 0.1 | 0.1 |
| % milk solids | 10.45 | 9.96 | 11.01 | 11.01 | 10.95 |
| ratio, milk solids/alcohol | 0.66 | 0.53 | 0.88 | 0.88 | 0.87 |

All the compositions were found to possess the desirable hair-bonding and skin cooling effects of the composition of Example 1, and all were storage-stable and non-flammable.

While particular examples of the present invention have been shown and described, it is apparent that changes and modifications may be made therein without departing from the invention in its broadest aspects. The aim of the appended claims, therefore, is to cover all such changes and modifications as fall within the true spirit and scope of the invention.

Having thus described my invention, what is claimed is:

1. A homogeneous non-flammable fluid composition consisting essentially of the following ingredients in their respective amounts:

| Ingredient | Parts by Weight |
|---|---|
| cow's milk solids | 15–30 |
| water | 140–180 |
| ethanol | 15–35 |
| pharmacologically safe volatile fragrance | 0.1–1.0 | wherein said milk solids constitute between 5% and 15% by weight of the composition, said composition being useful in providing a bonding effect to human hair and a cooling and antiseptic effect to human skin, and being resistant to microbial degradation for at least a year at ambient room temperatures, said composition having been made under conditions wherein, at the instant of admixture of the ingredients, the composition contains at least 20% water to avoid formation of an irreversible precipitate.

2. The composition of claim 1 wherein the ratio of milk solids to ethanol is between 0.5 and 1.5.

3. The composition of claim 1 wherein the milk solids are provided by dairy cow's milk having a fat content below 2%.

4. The composition of claim 1 which remains homogeneous for one to three years at ambient room temperature, and longer if refrigerated.

5. The composition of claim 1 made by the slow addition of absolute ethanol to liquid milk, with good stirring.

6. The composition of claim 1 made by the slow addition of liquid milk to ethanol containing at least 20% water, with continuous stirring.

* * * * *